United States Patent [19]
Paik et al.

[11] Patent Number: 5,739,120
[45] Date of Patent: Apr. 14, 1998

[54] TREATMENT OF VIRAL INFECTIONS BY ADMINISTRATION OF α-[1-(3-ALKYLTHIO-3-DEOXY-2-O-ACYLGLYCERYL)]-ω[5'-(9-ARABINOSYLPURINYL)] DIPHOSPHATES OR PURINE ISOSTERS THEREOF

[75] Inventors: Woo Hyun Paik, Seoul; Won Sup Shin, Kyungki-Do; Jae Seung Lee, Seoul; Hee Sang Chai, Kyungki-Do, all of Rep. of Korea

[73] Assignee: Boryung Pharmaceutical Co., Ltd., Seoul, Rep. of Korea

[21] Appl. No.: 837,275

[22] Filed: Apr. 30, 1997

Related U.S. Application Data

[63] Continuation of Ser. No. 353,291, Dec. 5, 1994, abandoned.

[30] Foreign Application Priority Data

Dec. 4, 1993 [KR] Rep. of Korea .................... 93-26496

[51] Int. Cl.$^6$ .................................................... A61K 31/70
[52] U.S. Cl. .......................... 514/47; 514/48; 536/26.22; 536/26.23
[58] Field of Search ................. 514/47, 48; 536/26.22, 536/26.23

[56] References Cited

U.S. PATENT DOCUMENTS

| | | | |
|---|---|---|---|
| 3,321,463 | 5/1967 | Moffatt | 536/26.23 |
| 3,787,392 | 1/1974 | Bergmeyer et al. | 536/26.22 |
| 3,803,125 | 4/1974 | Bergmeyer et al. | 536/26.22 |
| 3,872,083 | 3/1975 | Okutsu et al. | 536/26.23 |
| 4,291,024 | 9/1981 | Turcotte | 514/47 |
| 4,471,113 | 9/1984 | MacCoss et al. | 536/26.22 |
| 4,622,392 | 11/1986 | Hong et al. | 536/26.22 |
| 5,159,067 | 10/1992 | Schinazi et al. | 536/26.23 |

FOREIGN PATENT DOCUMENTS

| | | |
|---|---|---|
| 3543346 | 6/1986 | Germany . |
| 4026265 A1 | 2/1992 | Germany . |
| 7104160 | 10/1971 | Netherlands . |
| 0671290 | 3/1980 | U.S.S.R. . |
| WO 86/00309 | 1/1986 | WIPO . |
| WO 91/19726 | 12/1991 | WIPO . |

OTHER PUBLICATIONS

MacCoss et al., "The Synthesis, Characterization and Preliminary Biological Evaluation of 1-β-D-Arabinofuranosylcytosine-5'-Diphosphate-L-1, 2-dipalmitin," *Biochem. Biophys. Res. Comm.*, 85(2), 714–723 (1978).

Ryu et al., "Phospholipid-Nucleoside Conjugates. 3. Synthesis and Preliminary Biological Evaluation of 1-β-D-Arabinosylcytosine 5'-Diphosphate-L-1,2-dipalmitin and Selected 1-β-D-Arabinosylcytosine 5'-Diphosphate-L-1,2-Diacylglycerols," *J. Med. Chem.*, 25(11), 1322–1329 (1982).

Kumar et al., "Equal Inhibition of HIV Replication by Stereoisomers of Phosphatidyl-Azidothymidine," *J. Biol. Chem.*, 267(28), 20288–20292 (1992).

Matsushita et al., "Phospholipid Derivatives of Nucleoside Analogs as Prodrugs with Enhanced Catabolic Stability," *Cancer Research*, 41(7), 2707–2713 (1981).

Scheit, "Nucleotide Analogs. Synthesis and Biological Function," John Wiley & Sons, New York, NY, 1980, pp. 211–218.

Turcotte et al.(I), "Cytotoxic Liponucleotide Analogs. I. Chemical Synthesis of CDP-Diacylglycerol Analogs Containing the Cytosine Arabinoside Moiety," *Biochim. Biophys. Acta*, 619, 604–618 (1980).

Turcotte et al.(II), "Cytotoxic Liponucleotide Analogs. II. Antitumor Activity of CDP-Diacylglycerol Analogs Containing the Cytosine Arabinoside Moiety," *Biochim. Biophys. Acta*, 619, 619–631 (1980).

Claude Piantadosi et al. "Synthesis and Evaluation of Novel Ether Lipid Nucleoside Conjugates for Anti-HIV-1 Activity", J. Med. Chem. 1991, pp. 1408–1414., V. 34, Issue No. 4.

Louis S. Kucera et al., "Novel Membrane-Interactive Ether Lipid Analogs That Inhibit Infectious HIV-1 Production and Induce Defective Virus Formation", AID Research and Human Retroviruses, vol. 6, Apr., 1990, pp. 491–501.

*Primary Examiner*—John Kight
*Assistant Examiner*—L. Eric Crane
*Attorney, Agent, or Firm*—Jacobson, Price, Holman & Stern, PLLC

[57] ABSTRACT

The present invention relates to new liponucleotide analog compounds having useful antiviral activity, represented by general formula (I):

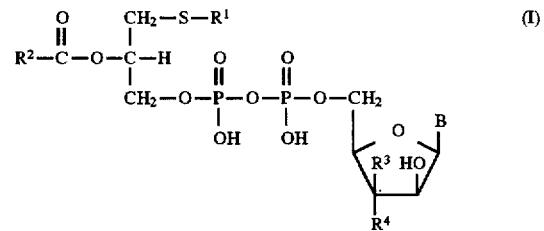

wherein $R^1$ is a saturated or unsaturated alkyl having 6–22 C atoms; $R^2$ is a saturated or unsaturated alkyl having 12–20 C atoms; $R^3$ and $R^4$ are each hydrogen or hydroxy; and B is one of the nucleoside bases of formula (a):

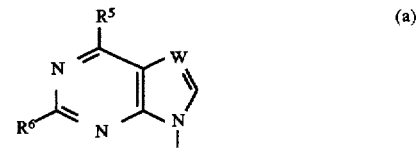

wherein $R^5$ is a hydrogen, halogen, hydroxy, amino, mercapto, or $C_1$–$C_4$ alkyl amino; $R^6$ is a hydrogen, halogen or amino; W is a nitrogen or C—$R^8$ where $R^8$ is hydrogen, halogen, amino or $C_1$–$C_4$ alkyl, and pharmaceutically acceptable salts thereof.

9 Claims, 2 Drawing Sheets

TREATMENT OF VIRAL INFECTIONS BY ADMINISTRATION OF α-[1-(3-ALKYLTHIO-3-DEOXY-2-O-ACYLGLYCERYL)]-ω[5′-(9-ARABINOSYLPURINYL)] DIPHOSPHATES OR PURINE ISOSTERS THEREOF

This is a continuation of Ser. No. 08/353,291, filed on Dec. 5, 1994, abandoned.

BACKGROUND OF THE INVENTION

(1) Field of the Invention

The present invention relates to new liponucleotide analog compounds having useful antiviral activity, represented by general formula (I):

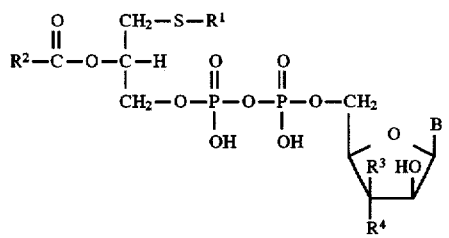

wherein $R^1$ is a saturated or unsaturated alkyl having 6–22 C atoms; $R^2$ is a saturated or unsaturated alkyl having 12–20 C atoms; $R^3$ and $R^4$ are each hydrogen or hydroxy; and B is one of the nucleoside bases of formula (a):

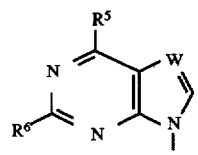

wherein $R^5$ is a hydrogen, halogen, hydroxy, amino, mercapto, or $C_1$–$C_4$ alkyl amino; $R^6$ is a hydrogen, halogen or amino; W is a nitrogen or C—$R^8$, where $R^8$ is hydrogen, halogen, amino or $C_1$–$C_4$ alkyl, and pharmaceutically acceptable salts thereof.

The present invention also relates to methods of preparing and using the compounds and to pharmaceutical compositions containing effective amounts of such compounds.

The compounds of formula (I), consisting of 1-S-alkyl phospholipid and nucleoside, may be D-form or L-form in its phospholipid portion or the mixture thereof.

(2) Description of the Prior Art

Liponucleotides, consisting of nucleoside and phospholipid have been synthesized to allow the nucleosides to be delivered efficiently to cancer or virus infected cells and thereby increase their antiviral effect. Diacyl-glycero-nucleoside compounds, for instance, have been produced by reacting nucleoside-5′-monophosphomorpholidate with 1,2-diacyl glycero-3-phosphate [Journal of Medical Chemistry 25, 1322 (1982); Biochemical and Biophysical Research Communication 85, 715 (1978); Biochimica et Biophysic Acta 619, 604 (1980)].

In addition, a compound consisting of 1-O-alkyl-2-O-acyl-glycero-3-phosphate and nucleoside, wherein the phospholipid having anticancer and immune modulating activity was expected to give synergistic or at least additive effect together with the nucleoside, has been disclosed in Korean Patent Publication No. 93/1988.

Considering tolerance or resistance to certain kinds of anticancer or antiviral agents and adverse effects thereby, however, a need continues for novel and improved antiviral and/or anticancer compounds.

SUMMARY OF THE INVENTION

Accordingly, it is an objective of the present invention to provide a novel antiviral agent having unique molecular structure and useful physicochemical properties. The objective is attained according to the present invention by providing 1-S-alkyl-phosphoryl-nucleosides of the general formula (I).

DETAILED DESCRIPTION OF THE INVENTION

Figure 1:
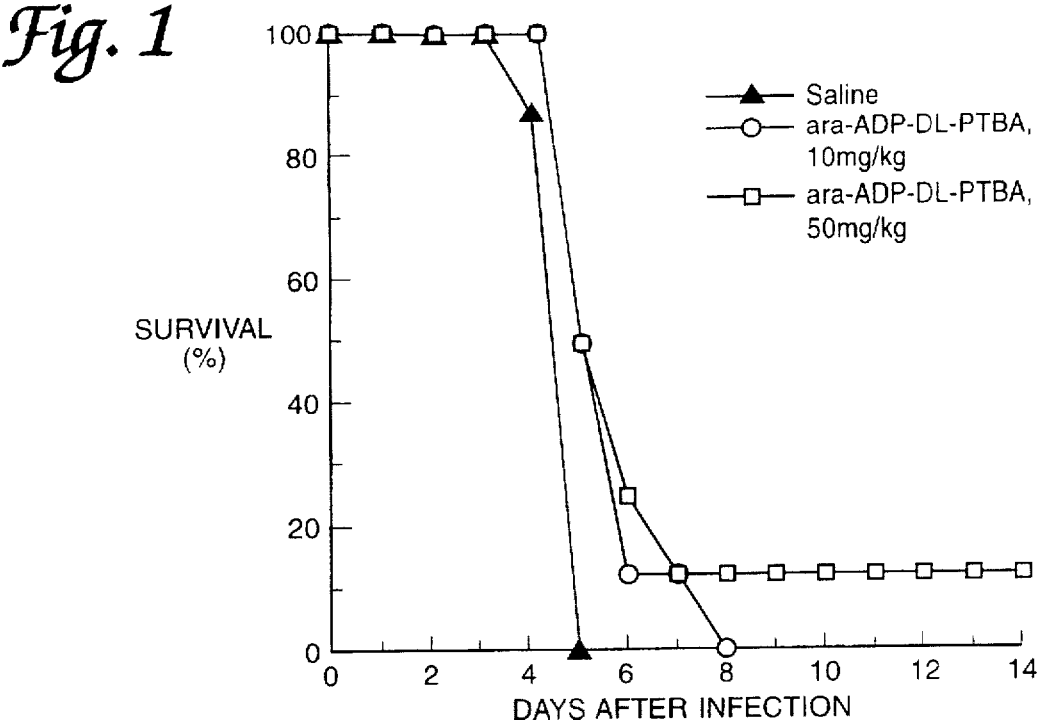
FIG. 1 illustrates survival rate of mice having been infected with Herpes Simplex Virus Type-1 and then intravenously administered with ara-ADP-DL-PTBA of the invention.

The compounds (I) of the present invention can be prepared by either method as illustrated in reaction scheme 1 or 2.

[REACTION SCHEME 1]
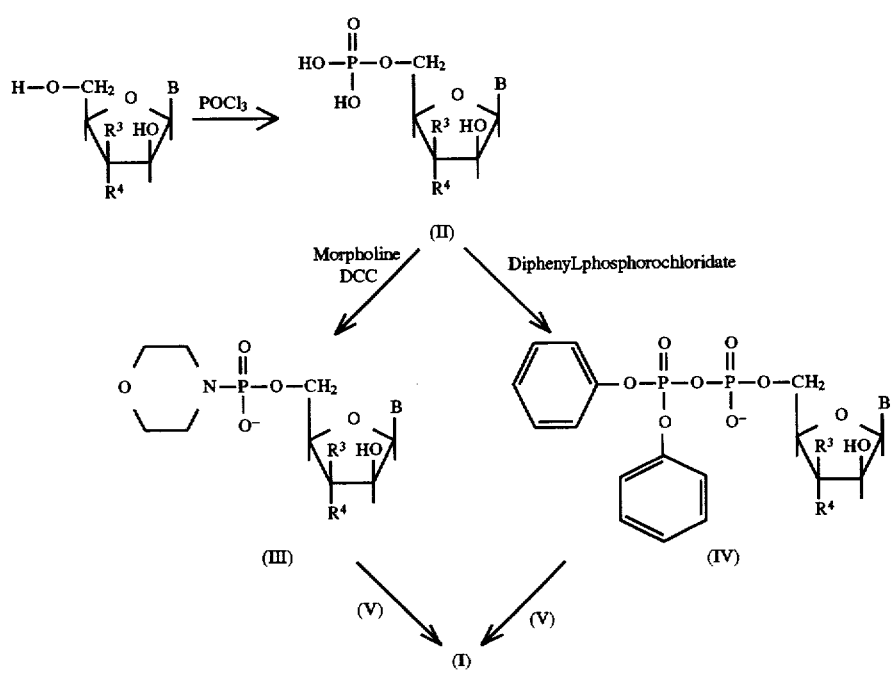
[REACTION SCHEME 2]
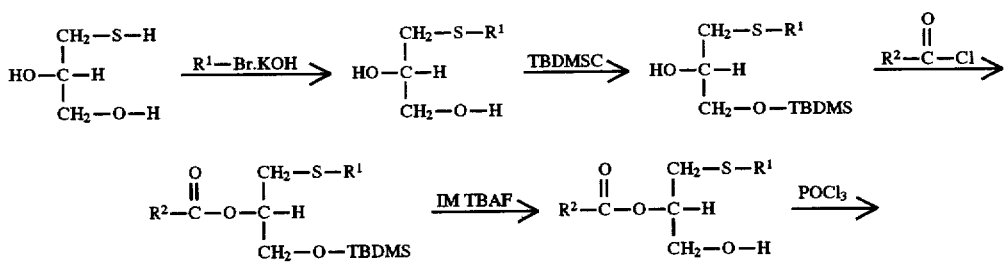

-continued
[REACTION SCHEME 2]

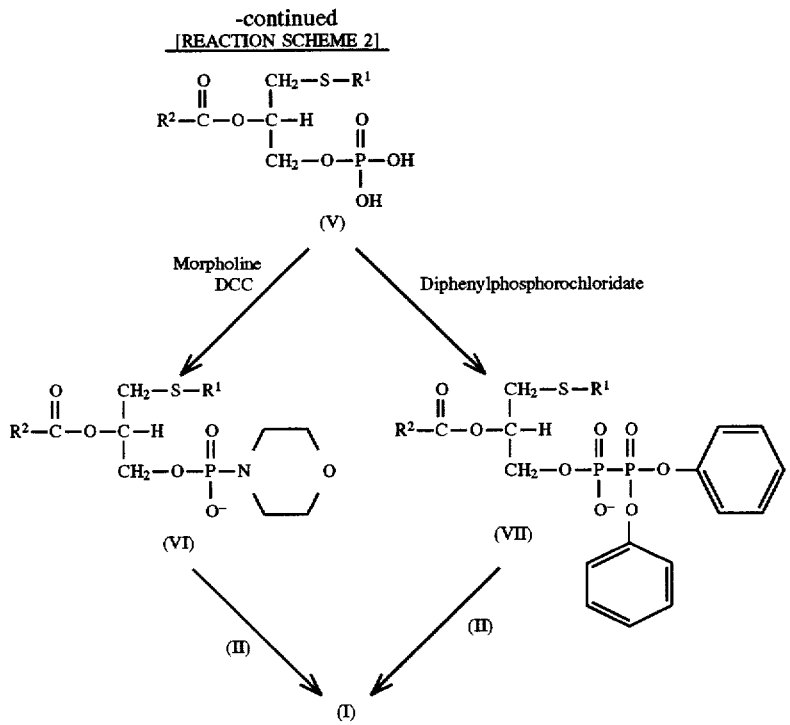

wherein $R^1$, $R^2$, $R^3$, $R^4$ and B represent the same radicals as defined in formula (I), and DCC, TBDMSC and TBAF are understood to designate N,N'-dicyclohexylcarbodiimide, tert-butyl-dimethyl silyl chloride and tetra-butyl ammonium fluoride, respectively.

According to reaction scheme 1, the compounds (I) can be obtained by reaction of 1-S-alkyl-2-O-acyl-l-thioglycerol-3-phosphates (V) with morpholidates (III) or with $P^1$-nucleoside-5'-$P^2$-diphenyl pyrophosphates (IV) which have been prepared from nucleotides (II).

According to reaction scheme 2, the compounds (I) can be obtained by reaction of nucleotides (II) with morpholidates (VI) or with $P^1$-glycerol-5'-$P^2$-diphenyl pyrophosphates (VII) which have been prepared from phospholipids (V).

The liponucleotide compound of the present invention exerts its effect on virus-infected cells by way of nucleoside or nucleotide released therefrom by enzymatic cleavage. Nucleotides thus released may be effective even on nucleoside resistant cells lacking in nucleoside kinase activity.

Since phospholipid itself as well as nucleoside gets involved in platelet aggregation, hypersensitivity, inflammation, etc. and it is also known as a useful prophylactic and/or therapeutic agent for circulatory disorder, allergy and neoplastic disease, the liponucleotide compound of the present invention is expected to have additive or synergistic effect.

As long as the nucleoside or nucleotide remains in the compound (I) of the present invention, —$NH_2$ group in the base can be protected from removal by deaminase. Accordingly, even more nucleoside or nucleotide in the compound of the present invention may have access to target cells when compared with simple nucleoside or nucleotide. The antiviral effect of the compound (I) can be further enforced by forming liposome through the phospholipid portion of the compound.

Since the phospholipid confers lipophilicity on the compound (I) of the present invention, it is quite able to permeate through bio-membranes. The compounds (I) may be taken up into the cells having phospholipid binding sites.

The compounds (I) of the present invention can be converted into pharmaceutically acceptable salts and can be used for preparing liquid formulations like injection.

The compounds (I) and the salts thereof can be employed in mixture with pharmaceutically acceptable organic or inorganic carriers suitable for pharmaceutical formulations—for instance, injections, emulsions, suspensions, capsules, granules, pulvis, tablets and pills. Pharmaceutically acceptable carriers may include auxiliaries such as excipient, dispersant, stabilizer, preservatives, wetting agents and emulsifier, colorants, buffers and/or fillers.

The compounds consisting of 1-S-alkyl phospholipids and nucleosides according to the present invention and the salts thereof exhibit excellent antiviral activity when compared with simple nucleosides since they are rarely inactivated by metabolism and readily permeable through bio-membranes.

The present invention is further described in the following preferred embodiments. While the invention is exemplified in the following, such are not intended to limit the scope of the present invention.

PREFERRED EMBODIMENTS

EXAMPLE 1

Racemic (abbreviated herein as "rac")-1-S-octadecyl-1-thioglycerol 3-mercapto-1,2-propanediol (13.63 g; 126 mM) was dissolved in 70 ml of methanol and a solution of 27.67 g (83 mM) of stearylbromide in 140 ml of hexane was added thereto.

Subsequently, 216 ml of 1N KOH-$CH_3OH$ was added dropwise for an hour with stirring at room temperature. After stirring for an additional 24 hours, the mixture was cooled to 10° C. and filtered under reduced pressure.

The filtrate was washed with methanol and with water to give 27 g of the subject material (yield: 90%, m.p: 75°–77° C.). The material was analyzed with results as follows:

$^1$H NMR(200 MHz, CDCl$_3$)

δ 0.80–0.95(3H, t, CH$_3$), 1.05–1.95(32H, m, 16CH$_2$), 2.45–2.85 (4H, m, CH$_2$SCH$_2$), 3.42–3.90 (3H, m, 2-CH, 3-CH$_2$)

EXAMPLE 2 rac-1-S-octadecyl-3-O-(tert-butyldimethylsilyl)-1-thioglycerol

The product of example 1 (18 g ;50 mM), tert-butyldimethylsilyl chloride (9.04 g ;60 mM) and imidazol (8.17 g; 120 mM) were added to 100 ml of N,N-dimethyl formamide. The mixture was stirred at room temperature for 28 hours and evaporated at 40° C. under reduced pressure to remove solvent therefrom. The residue was extracted with the mixed solution of ether (100 ml) and water (100 ml). The organic layer was dried over Na$_2$SO$_4$, filtered and evaporated to give 22.28 g of the oily subject material (yield 94%).

EXAMPLE 3 rac-1-S-octadecyl-2-O-palmitoyl-3-O-(tert-butyldimethylsilyl)-1-thioglycerol

The product of example 2 (21 g; 44.2 mM) and pyridine (4.65 g; 58.8 mM) were added to 112 ml of toluene. Palmitoyl chloride (14.59 g; 53.1 mM) was further added dropwise for an hour and then stirred for 20 hours at room temperature.

The reaction mixture was extracted with the solution of ether (56 ml) and water (56 ml). The organic layer thus produced was washed consecutively with 28 ml of 0.5N sulfuric acid, with 28 ml of saturated NaHCO$_3$ solution and with 28 ml of water. The resulting solution was dried over Na$_2$SO$_4$ and evaporated under reduced pressure to give 30.28 g of the subject material (yield: 96%). The material was analyzed with results as follows:

$^1$H NMR(200 MHz, CDCl$_3$)

δ 0.10(6H, S, (CH$_3$)$_2$Si), 0.70–1.00(15H, m, 2CH$_3$, (CH$_3$)$_3$C), 1.10–1.90(58H, m, 29CH$_2$), 2.22–2.80(6H, m, CH$_2$SCH$_2$, CH$_2$CO), 3.76–3.94(2H, d, 3-CH$_2$), 4.90–5.10(1 h, q, 2-CH)

EXAMPLE 4 rac-1-S-octadecyl-2-O-palmitoyl-1-thioglycerol

A mixture of the product of example 3 (28 g; 39.3 mM) acetic acid (5.67 ml) and tetrahydrofuran (84 ml) was stirred for 10 minutes. 58.9 ml of 1M tetrabutylammonium fluoridetetrahydrofuran was added dropwise thereto at 15°–18 ° C. for an hour and stirred further at room temperature for 20 hours.

The stirred mixture was evaporated at 30° C. under reduced pressure to remove solvent therefrom. 70 ml of acetonitrile and 70 ml of 95% ethanol were added to the residue, and the resulting mixture was warmed to 40° C., allowed to cool at room temperature and subsequently cooled to 0° C. After stirring for 2 hours, the solution was filtered under reduced pressure to give white precipitate, to which 700 ml of 95% ethanol was added. The mixture was warmed and refluxed for 5 minutes, stirred overnight to cool to room temperature, further stirred at 20° C. for 5 hours and then filtered under reduced pressure. The filtered solution was concentrated to half of the volume under reduced pressure, stirred at 0° C. for 3 hours and filtered under reduced pressure to give 12.46 g of the subject material (yield: 53%, m.p: 42°–45° C.). The material was analyzed with results as follows:

$^1$H NMR(200 MHz, CDCl$_3$)

δ 0.80–0.95(6H, t, 2CH$_3$), 1.10–1.90(58H, m, 29CH$_2$), 2.26–2.44(2H, t, CH$_2$CO), 2.50–2.64(2H, t, SCH$_2$), 2.68–2.82(2H, d, 1-CH$_2$), 3.76–3.94(2H, d, 3-CH$_2$), 4.90–5.10(1H, q, 2-CH)

EXAMPLE 5 rac-1-S-octadecyl-2-O-palmitoyl-1-thioglycerol-3-phosphate

A mixture of phosphoryl chloride (3.97 g; 25.9 mM) and hexane (9.6 ml) was cooled to 0° C. and thereto 2.62 g (25.9 mM) of trimethylamine in 9.6 ml of hexane was added dropwise for 20 minutes. After the mixture was stirred at 0° C. for 20 minutes, 10.68 g (17.8 mM) of the product of example 4 dissolved in 96 ml of toluene was added dropwise at 0°–5° C. for 1 hour, and the resulting mixture was stirred further at 20°–25° C. for 5 hours. 9.6 ml of water was added to the mixture and stirred for an hour. The solution thus obtained was worked up with 192 ml of ether and with 48 ml of H$_2$O. The organic layer was separated, dried over Na$_2$SO$_4$ and concentrated at 30° C. under reduced pressure to remove solvent therefrom. The residue was dissolved in 192 ml of acetone, stirred for 30 minutes at room temperature and for 2 hours at 0° C., and then filtered under reduced pressure to give 7.38 g of the subject material (yield 61%, m.p.: 64°–66° C.). The material was analyzed with results as follows:

$^1$H NMR(200 MHz CDCl$_3$)

δ 0.80–0.95(6H, t, 2CH$_3$), 1.10–1.90(58H, m, 29CH$_2$), 2.26–2.44(2H, t, CH$_2$CO), 2.50–2.64(2H, t, SCH$_2$), 2.68–2.82(2H, d, 1-CH$_2$), 4.04–4.55(2H, m, 3-CH$_2$), 5.04–5.22(1H, m, 2-CH)

EXAMPLE 6 rac-1-S-hexadecyl-2-O-palmitoyl-1-thioglycerol-3-phosphate

The same procedure as described in example 1 to 5 was employed except cetylbromide was used instead of stearylbromide to produce the subject material (yield; 56%, m p; 68°–71° C.). The material was analyzed with results as follows:

$^1$H NMR(200 MHz, CDCl$_3$)

δ 0.80–0.95 (6H, t, 2CH$_3$), 1.10–1.90 (54H, m, 27CH$_2$) , 2.26–2.44(2H, t, CH$_2$CO), 2.50–2.64(2H, t, SCH$_2$), 2.68–2.82(2H, d,1-CH$_2$), 4.04–4.55(2H, m, 3-CH$_2$), 5.04–5.22(1H, m, 2-CH)

EXAMPLE 7

9-β-D-arabinofuranosyladenine-5'-monophosphate<ara-AMP>

A mixture of acetonitrile (50 ml), phosphoryl chloride (16 ml ;172 mM) and pyridine (15.6 ml; 193 mM) was cooled to 0° C. and 2 ml of water was added thereto. After stirring for 40 minutes at 0° C., 10.68 g (40 mM) of vidarabine (abbreviated herein as "ara-A") was added. After stirring at 0°–5° C. for 6 hours, 900 ml of ice water was added. The resulting solution was adjusted to pH 7.0 with conc-NH$_3$

9 solution and concentrated under reduced pressure. The residue was dissolved in 900 ml of water, adsorbed onto AG 1-X8 (Formate) column (5×50 cm) and eluted with 2000 ml of water and with 5000 ml of 0.5N formic acid. The 1 to 3000 ml eluted fraction of formic acid solution was collected and concentrated below 30° C. to produce white crystals. The white product was cooled to 0° C., stirred for 2 hours, filtered under reduced pressure and washed with acetone to give 12.22 g of the subject material (yield; 88%, m.p.: 187°–189° C.)

EXAMPLE 8

9-β-D-arabinofuranosyladenine-5'-diphosphate-rac-1-S-octadecyl-2-O-palmitoyl-1-thioglycerol <ara-ADP-DL-PTBA>.

Morpholine (2.09 ml; 24 mM) and ara-AMP (2.08 g; 6 mM) produced through the example 7 were added to the mixed solution of 70 ml of water and 70 ml of tert-butanol. The mixture was warmed to 50°–55° C. and thereto 4.95 g (24 mM) of N,N'-dicyclohexylcarbodiimide dissolved in 100 ml of tert-butanol was added dropwise.

The resulting mixture was refluxed for 8 hours, stirred overnight at room temperature, filtered to remove precipitate therefrom and concentrated under reduced pressure to a volume of 50 ml. The suspension was extracted twice with 150 ml of ether. The aqueous layer thus produced was separated and concentrated under reduced pressure. The residue was mixed with ether, stirred overnight, concentrated under reduced pressure and dried to give 3.95 g of 9-β-D-arabinofuranosyladenine-5'-monophosphoromorpholidate-4-morpholine-N,N'-dicyclohexyl carboximidium salt (yield: 93%).

The compound (2.78 g ;3.9 mM) and rac-1-S-octadecyl-2-O-palmitoyl-1-thioglycerol-3-phosphate (2.67 g ;3.9 mM) obtained in example 5 which had been distilled as an azeotropic mixture with pyridine and dried, were dissolved in 250 ml of dry pyridine and then stirred at room temperature for six days to complete reaction.

The resulting mixture was evaporated to remove pyridine primarily and distilled as an azeotropic mixture with toluene to remove traces of pyridine. The residue was dissolved in the mixed solution of glacial acetic acid (30 ml) and chloroform-methanol-water (2:3:1; 300 ml), stirred at room temperature for 2 hours, and 500 ml of chloroform was added thereto. The organic layer was separated, concentrated under reduced pressure and distilled four times as an azeotropic mixture with 15 ml of toluene to remove therefrom traces of glacial acetic acid.

The residue was dissolved in 200 ml of chloroform-methanol-water (2:3:1), adsorbed onto a DE-12 (acetate) cellulose column (5×60 cm), eluted and fractionated with 5000 ml of chloroform-methanol-water (2:3:1) solution having linear NH$_4$OAc concentration gradient from 0 to 0.15M. 1800 to 2,900 ml of the fractionated solution was concentrated under reduced pressure to produce white crystals, which were cooled to 0° C., stirred for 3 hours, filtered under reduced pressure and washed with water. The product thus obtained was converted to its sodium salt by dissolving in chloroform-methanol-water (2:3:1) solution, eluting through an Amberite CG-50 (Na$^+$) column (5×60 cm) and evaporating the eluent. The residue was crystallized with acetone and chloroform, filtered and dried in vacuo over P$_2$O$_5$ to give 1.72 g of the subject material (yield 42%, m.p.: 197°–200° C.). The material was analyzed with results as follows:

$^1$H NMR(200 MHz, CDCl$_3$-CD$_3$OD-D$_2$O=2:3:1)

10

δ 0.80–0.95(6H, t, 2CH$_3$), 1.10–1.90(58H, m, 29CH$_2$), 2.25–2.45(2H, t, CH$_2$CO), 2.50–2.60(2H, t, SCH$_2$), 2.75–2.90(2H, d, 1-CH$_2$), 4.02–4.65(7H, m, 3-CH$_2$, H-2', H-3', H-4', H-5'), 5.07–5.15(1H, m, 2-CH), 6.35–6.45(1H, d, H-1'), 8.20(1H, S, adenine H-2), 8.50(1H, S, adenine H-8)

| Elemental analysis C$_{47}$H$_{85}$N$_5$O$_{12}$P$_2$SNa$_2$ | | | | |
|---|---|---|---|---|
| | C | H | N | S |
| Theoretical: | 53.65 | 8.14 | 6.65 | 3.05 |
| Found: | 52.82 | 9.05 | 6.48 | 2.86 |

EXAMPLE 9

9-β-D-Arabinofuranosyladenine-5'-diphosphate-rac-1-S-hexadecyl-2-O-palmitoyl-thioglycerol <ara-ADP-DL-PTCA>

The same procedure as described in example 8 was employed except rac-1-S-hexadecyl-2-O-palmitoyl-1-thioglycerol-3-phosphate was used instead of rac-1-S-octadecyl-2-O-palmitoyl-1-thioglycerol-3-phosphate to produce the subject material (yield; 48%, m.p.; 201°–206° C.). The material was analyzed with results as follows;

$^1$H NMR(200 MHz, CDCl$_3$-CD$_3$OD-D$_2$O=2:3:1)

δ 0.80–0.95(6H, t, 2CH$_3$), 1.10–1.90(54H, m, 27CH$_2$) 2.25–2.45(2H, t, CH$_2$CO), 2.50–2.60(2H, t, SCH$_2$), 2.75–2.90(2H, d, 1-CH$_2$), 4.02–4.65(7H, m, 3-CH$_2$, H-2', H-3', H-4', H-5'), 5.07–5.15(1H, m, 2-CH), 6.35–6.45(1H, d, H-1'), 8.20(1H, S, adenine H-2), 8.50(1H, S, adenine H-8)

| Elemental analysis: C$_{45}$H$_{81}$N$_5$O$_{12}$P$_2$SNa$_2$ | | | | |
|---|---|---|---|---|
| | C | H | N | S |
| Theoretical; | 52.77 | 7.97 | 6.84 | 3.13 |
| Found; | 52.64 | 8.13 | 6.57 | 2.92 |

EXAMPLE 10

9-β-D-arabinofuranosyladenine-5'-diphosphate-rac-1-S-octadecyl-2-O-palmitoyl-2-thioglycerol <ara-ADP-DL-PTBA>

A solution of 5.77 g (28 mM) of N,N'-dicyclohexylcarbodiimide (DCC) in 100 ml of tert-butanol was added dropwise to the refluxed mixture of rac-1-S-octadecyl-2-O-palmitoyl-1-thioglycerol-3-phosphate (4.07 g ;6 mM), morpholine (2.44 ml; 28 mM) and tert-butanol (70 ml). The resulting mixture was refluxed for 5 hours and stirred overnight at room temperature. 30 ml of water was added, and the resulting solution was stirred for 3 hours to decompose excess DCC and filtered to remove white crystals therefrom. The filtrate was concentrated under reduced pressure and extracted with ether. The extract thus obtained was concentrated under reduced pressure. The residue was distilled three times as an azeotropic mixture with toluene and then dried.

Subsequently, 2.71 g (7.8 mM) of ara-AMP and 6.82 ml (15.6 mM) of trioctylamine were added to the resulting product. The mixture was distilled four times as an azeotropic mixture with pyridine and dried. The dried product was dissolved in 300 ml of pyridine and stirred at room temperature for 8 days. The resulting mixture was concentrated under reduced pressure to remove pyridine primarily and distilled three times as an azeotropic mixture with toluene to remove traces of pyridine. The residue was dissolved in 450 ml of the mixed solution of glacial acetic acid (45 ml) and chloroform-methanol-water (2:3:1), stirred at room temperature for an hour, and 750 ml of chloroform was added thereto. The organic layer thus produced was separated, concentrated under reduced pressure and distilled four times as an azeotropic mixture with toluene to remove trace amount of glacial acetic acid therefrom. The residue was dissolved in 200 ml of chloroform-methanol-water (2:3:1) solution and the solution was adsorbed onto a DE-52 (acetate) cellulose column (3×60 cm) according to the method as described in example 8, eluted and fractionated with chloroform-methanol-water (2:3:1) solution having linear $NH_4OAc$ concentration gradient from 0 to 0.15 M to give 2.15 g of the subject material (yield 34%). The material showed identical results in analysis as in example 8.

EXAMPLE 11

9-β-D-arabinofuranosyladenine-5'-diphosphate-rac-1-S-hexadecyl-2-O-palmitoyl-1-thioglycerol (ara-ADP-DL-PTCA)

ara-AMP (1.74 g; 5 mM) and trioctylamine (2.19 ml; 5 mM) were dissolved in 50 ml of methanol and the solution was concentrated under reduced pressure to remove solvent therefrom. The residue was dissolved in N,N-dimethyl formamide and concentrated under reduced pressure to remove therefrom traces of water. The dry ara-AMP-tri-O-octylammonium salt was dissolved in 60 ml of dioxane and in 30 ml of N,N-dimethyl formamide, and 1.5 ml (7.2 mM) of diphenylphosphorochloridate and 2.25 ml (9.4 mM) of tributylamine were added to the solution. The resulting mixture was allowed to react at room temperature for 6 hours and then concentrated under reduced pressure to give $P^1$-(9-β-D-arabinofuranosyl adenine-5'-yl)-$P^2$-diphenyl pyrophosphate. 12 ml of dioxane was added to the residue and the mixture was concentrated under reduced pressure to remove water therefrom. The residue thus obtained was again dissolved in 6 ml of dioxane. The resulting solution was admixed with 2.71 g (4.2 mM) of rac-1-S-hexadecyl-2-O-palmitoyl-1-thioglycerol-3-phosphate in 10 ml of pyridine, and the mixture was allowed to react at room temperature for 5 days and then concentrated under reduced pressure to remove solvent therefrom. The residue was dissolved in 600 ml of chloroform-methanol-water (2:3:1) solution, and the solution was adsorbed onto DE-52 (acetate) cellulose column (3.5×60 cm), eluted and fractionated according to the method as described in example 8 to give 1.53 g of the subject material (yield: 36%). The material showed identical results in analysis as in example 9.

ACTIVITY TEST

To evaluate antiviral activity of the liponucleotide of the present invention, the compound was administered to mice which have been infected with herpes simplex virus type-1, and body weight change and survival rate of the mice was monitored for a period of time.

BALB/C mice (female, 4 weeks) were infected with herpes simplex virus type-1 Miyanma strain (2,000 PFU/mouse, ip). The compounds to be tested were iv or orally administered to the mice for four days. Body weight change and survival rate of the mice were observed for 2 weeks.

iv administration: The compound was weighed by electronic balance and then suspended in saline. The suspension was exposed to ultrasonication for 20 minutes to ensure complete dissolution. The solution was filtered through 0.22 um membrane filter to exclude microorganisms therefrom. 10 mg/kg or 50 mg/kg of compound was administered and saline was administered to the controls.

Oral administration: The compound was weighed by electronic balance and suspended in 0.5% carboxymethyl cellulose (abbreviated herein to as "CMC") solution. 50 mg/kg or 250 mg/kg of the compound was administered to the test group; 125 mg/kg of ara-A (vidarabine) was administered for comparison group; 0.5% CMC was administered to controls.

Figure 2:
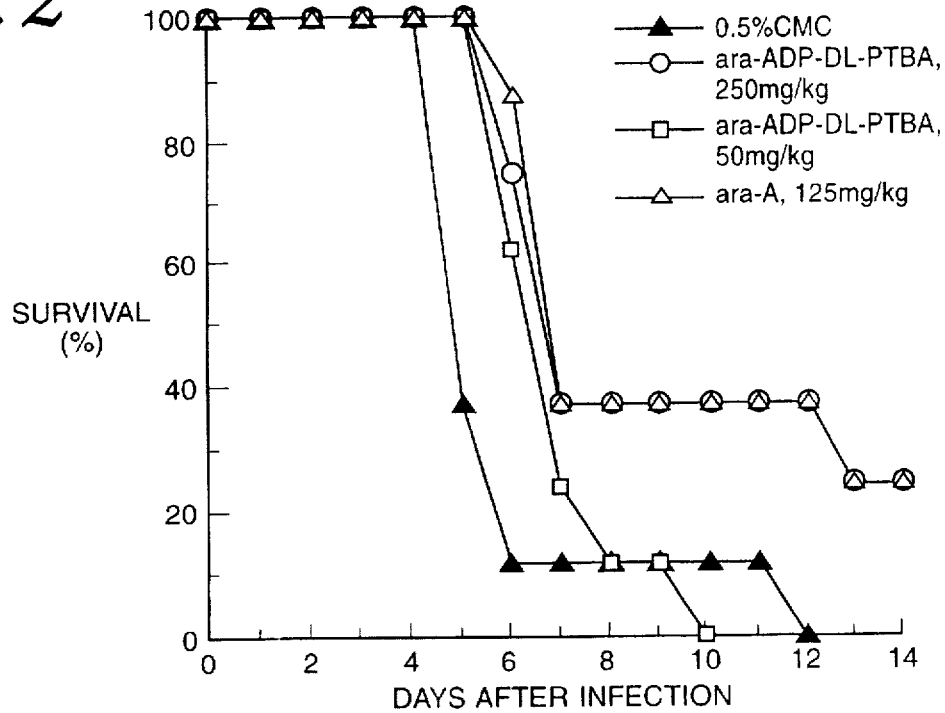
FIG. 2 illustrates survival rate of mice having been infected with Herpes Simplex Virus Type-1 and then orally administered with ara-ADP-DL-PTBA of the invention.
Figure 3:
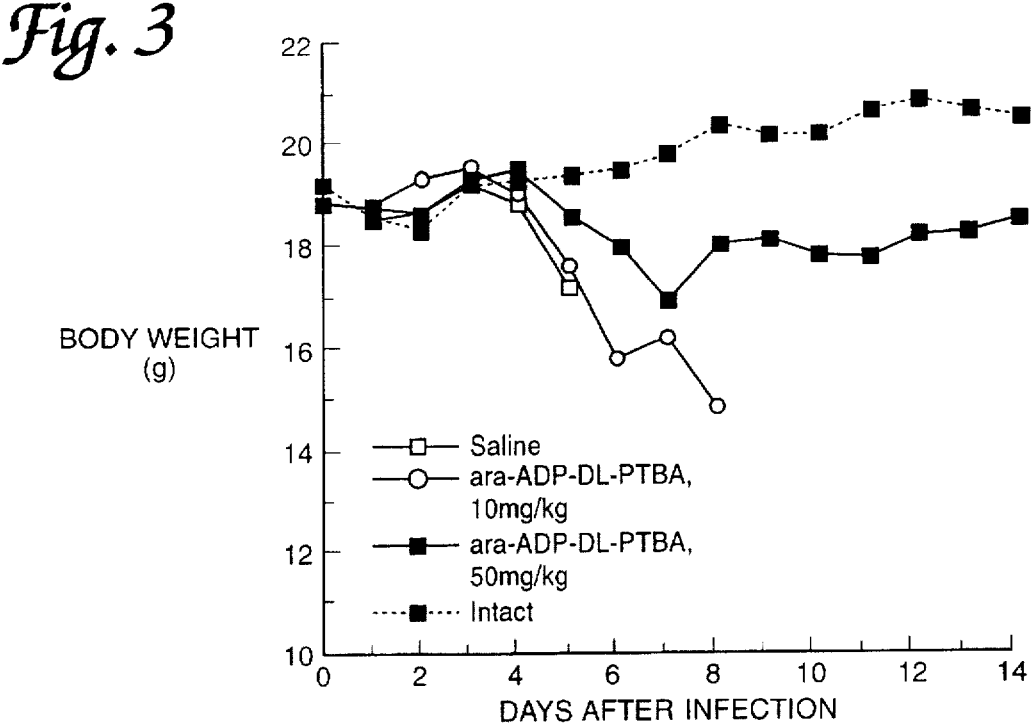
FIG. 3 illustrates body weight change of mice having been infected with Herpes Simplex Virus Type-1 and then intravenously administered with ara-ADP-DL-PTBA of the invention.
Figure 4:
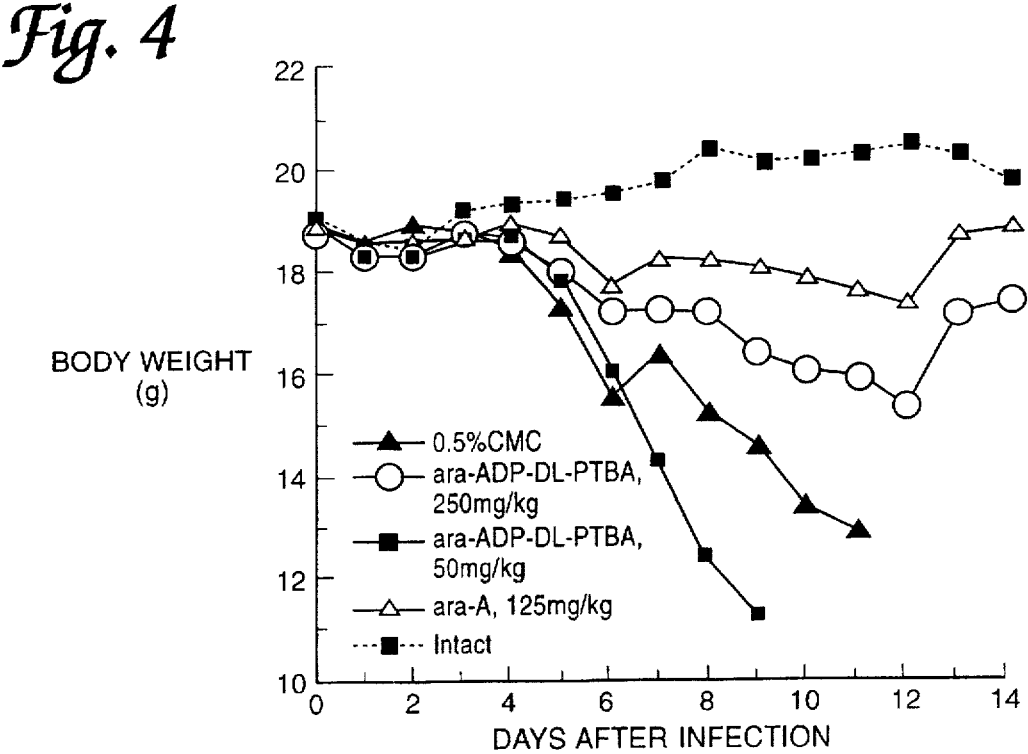
FIG. 4 illustrates body weight change of mice having been infected with Herpes Simplex Virus Type-1 and then orally administered with ara-ADP-DL-PTBA of the invention.

FIG. 1 and FIG. 2 show survival rate of the infected mice (% survival on vertical axis, days after infection on horizontal axis). FIG. 3 and FIG. 4 show body weight change of the infected mice (body weight on vertical axis, days after infection on horizontal axis).

As shown in FIG. 3 (iv administration), body weight decreased dramatically in controls around the 5th day and all of them were dead on the 6th day. In ara-ADP-DL-PTBA administered mice, body weight decreased rather slowly, specially in 50 mg/kg administered mice, compared with controls. In 50 mg/kg administered group, less mice were dead at the end of the time period (FIG. 1).

As shown in FIG. 4 (oral administration), body weight decreased noticeably from the 5th day from infection in 0.5% CMC treated controls and all of the mice were dead on the 12th day. In ara-ADP-DL-PTBA treated group, body weight also decreased from the 5th day from infection but rather slowly in 250 mg/kg treated group compared with controls. The 50 mg/kg of ara-ADP-DL-PTBA treated group showed similar body weight decrease as in controls within statistical error limit. ara-A treated group showed slower body weight decrease than controls and even than ara-ADP-DL-PTBA treated group.

In iv administration, 50 mg/kg of ara-ADP-DL-PTBA treated group showed higher survival rate than saline treated controls (FIG. 1). In oral administration, 250 mg/kg of ara-ADP-DL-PTBA treated group showed higher survival rate than 0.5% CMC treated controls (FIG. 2).

The data were analyzed by log-rank test and Wilcoxon test using statistical analysis system (SAS) to compare the survival time of ara-ADP-DL-PTBA treated group and controls (Table 1).

The results in table 1 support the conclusion that iv ara-ADP-DL-PTBA (10 mg/kg and 50 mg/kg) treated groups survived significantly longer within 5% error limit and ara-ADP-DL-PTBA can be used as an antiviral agent, especially for herpes simplex virus type 1 infection by intravenous route.

TABLE 1

Comparison of the survival time of ara-ADP-DL-PTBA treated group and controls by means of survival time test, log-rank test and Wilcoxon test.

| iv administration | | | oral administration | | |
|---|---|---|---|---|---|
| Drug (Dose) | TEST | p value | Drug (Dose) | TEST | p value |
| ara-ADP-DL-PTBA (10 mg/kg) | LOG-RANK WILCOXON | 0.0198 0.0201 | ara-ADP-DL-PTBA (50 mg/kg) | LOG-RANK WILCOXON | 0.8382 0.3929 |
| ara-ADP-DL-PTBA (50 mg/kg) | LOG-RANK WILCOXON | 0.0198 0.0201 | ara-ADP-DL-PTBA (250 mg/kg) | LOG-RANK WILCOXON | 0.0537 0.0919 |
| | | | ara-A (125 mg/kg) | LOG-RANK WILCOXON | 0.0256 0.0371 |
| saline | | | CMC | | |

What is claimed is:

1. A method for treating a viral infection in a patient comprising treating the patient with an effective quantity of a liponucleotide compound of general formula (I):

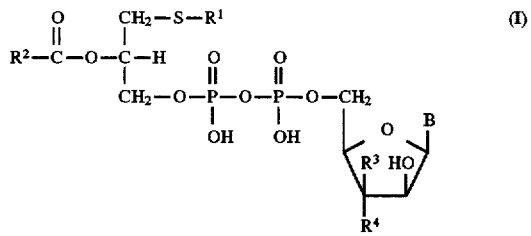

wherein $R^1$ is a saturated or unsaturated alkyl having 6–22 C atoms; $R^2$ is a saturated or unsaturated alkyl having 12–20 C atoms; $R^3$ and $R^4$ are each hydrogen or hydroxy; and B is one of the nucleoside bases of formula (a):

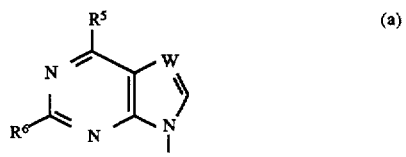

wherein $R^5$ is a hydrogen, halogen, hydroxy, amino, mercapto, or $C_1$–$C_4$ alkyl amino; $R^6$ is a hydrogen, halogen or amino; W is a nitrogen or C—$R^8$, where $R^8$ is hydrogen, halogen, amino or $C_1$–$C_4$ alkyl; or pharmaceutically acceptable salts thereof;

wherein said liponucleotide compounds and said pharmaceutically acceptable salts thereof are antiviral agents.

2. A method according to claim 1 wherein $R^1$ is a saturated or unsaturated alkyl group having 12–20 C atoms.

3. A method according to claim 1, wherein pharmaceutically acceptable salts thereof are sodium salts.

4. A method according to claim 2, wherein pharmaceutically acceptable salts thereof are sodium salts.

5. A method according to claim 1, wherein the compound of formula (I) is selected from the group consisting of:

a) 9-β-D-arabinofuranosyladenine-5'-diphosphate-rac-1-S-octadecyl-2-O-palmitoyl-2-thioglycerol;

b) 9-β-D-arabinofuranosyladenine-5'-diphosphate-rac-1-S-hexadecyl-2-O-palmitoyl-2-thioglycerol; and c) 9-β-D-arabinofuranosyladenine-5'-diphosphate-rac-1-S-tetradecyl-2-O-palmitoyl-2-thioglycerol; and pharmaceutically acceptable salts thereof.

6. A method according to one of claims 1–5 wherein the compound of formula (I) is combined with a pharmaceutically acceptable carrier or excipient.

7. A method according to claim 6, wherein the compound of formula (I) is enclosed in a capsule or provided as a solution suitable for administration by injection.

8. The method of treating according to claim 1 wherein the viral infection is a herpes simplex infection.

9. The method of treating according to claim 1 wherein the viral infection is a herpes simplex type-1 infection.

* * * * *